United States Patent [19]

Bailey

[11] Patent Number: 5,059,540
[45] Date of Patent: Oct. 22, 1991

[54] SEQUENTIAL C-TERMINAL DEGRADATION OF PEPTIDES AND PROTEINS USING CLEAVING REAGENTS SUCH AS SODIUM TRIMETHYLSILANOLATE OR TRIMETHYLAMINE N-OXIDE

[75] Inventor: Jerome M. Bailey, Duarte, Calif.

[73] Assignee: City of Hope, Duarte, Calif.

[21] Appl. No.: 576,943

[22] Filed: Aug. 13, 1990

[51] Int. Cl.$^5$ ............................................. G01N 33/68
[52] U.S. Cl. ..................................... 436/89; 530/345; 530/402; 530/408; 530/815
[58] Field of Search .................. 436/89; 530/345, 402, 530/408, 815, 816

[56] References Cited

U.S. PATENT DOCUMENTS 4,837,165  6/1989  Hawke .............................. 530/402 X
4,935,494  6/1990  Miller ................................. 436/89 X Primary Examiner—Robert J. Hill, Jr.
Attorney, Agent, or Firm—Edward S. Irons

[57] ABSTRACT

Reagents useful for the C-terminal sequencing of proteins and peptides are disclosed. The reagents include sodium trimethylsilanolate and trimethyl N-oxide. The reagents are used as cleaving reagents in a method for the sequential C-terminal degradation of peptides and proteins.

7 Claims, 6 Drawing Sheets

PEPTIDE THIOHYDANTOIN

+

AQUEOUS TFA

THIOHYDANTOIN LEUCINE

SHORTENED PEPTIDE

TRIMETHYLAMINE N-OXIDE

SEQUENTIAL C-TERMINAL DEGRADATION OF PEPTIDES AND PROTEINS USING CLEAVING REAGENTS SUCH AS SODIUM TRIMETHYLSILANOLATE OR TRIMETHYLAMINE N-OXIDE

This application is a continuation-in-part of Bailey application PCT/US90/02723 filed May 19, 1990, which is incorporated herein by reference.

FIELD OF THE INVENTION

This invention relates to the sequential degradation of peptides and proteins from the carboxy-terminus. More particularly, the invention relates to a method for the cleavage of the C-terminal thiohydantoin amino acid from the derivatized peptide which results from the use of a silylisothiocyanate as a coupling reagent in carboxy-terminal sequencing procedures.

BACKGROUND OF THE INVENTION

A. Background

The development of methods for the sequential degradation of proteins and peptides from the carboxy-terminus has been the objective of several studies. See Ward, C. W., *Practical Protein Chemistry—A Handbook* (Darbre, A., ed.) (1986) and Rangarajan, M., *Protein/Peptide Sequence Analysis: Current* (1988). Such a method would complement existing N-terminal degradations based on the Edman chemistry. Edman, P., *Acta.Chem.Scand.* 4:283-293 (1950). The most widely studied method and probably the most attractive because of its similarity to the Edman degradation has been the conversion of amino acids into thiohydantoins. This reaction, originally observed by Johnson and Nicolet, *J.Am.Chem.Soc.* 33:1973-1978 (1911), was first applied to the sequential degradation of proteins from the carboxy-terminus by Schlack and Kumpf, *Z.Physiol.Chem.* 154:125-170 (1926). These authors reacted ammonium thiocyanate, dissolved in acetic acid and acetic anhydride, with N-benzoylated peptides to form carboxyl-terminal 1-acyl-2-thiohydantoins. Exposure to strong base was used to liberate the amino acid thiohydantoin and generate a new carboxyl-terminal amino acid. The main disadvantages of this procedure have been the severity of the conditions required for complete derivatization of the C-terminal amino acid and for the subsequent cleavage of the peptidylthiohydantoin derivative into a new shortened peptide and an amino acid thiohydantoin derivative.

Since this work was published, numerous groups have tried to reduce the severity of the conditions required, particularly in the cleavage of the peptidylthiohydantoin, in order to apply this chemistry to the sequential degradation of proteins from the carboxyl terminal end. Lesser concentrations o sodium hydroxide than originally used by Schlack and Kumpf and of barium hydroxide were found to effectively cleave peptidylthiohydantoins. See Waley, S. G., et al., *J.Chem.Soc.* 1951:2394-2397 (1951); Kjaer, A., et al., *Acta Chem.Scand.* 6:448-450 (1952); Turner, R. A., et al., *Biochim.Biophys.Acta.* 13:553-559 (1954). Other groups used acidic conditions based on the original procedure used by Johnson and Nicolet for the deacetylation of amino acid thiohydantoins. See Tibbs, J., *Nature* 168:910 (1951); Baptist, V. H., et al., *J.Am.Chem.Soc.* 75:1727-1729 (1953). These authors added concentrated hydrochloric acid to the coupling solution to cause cleavage of the peptidylthiohydantoin bond. Unlike hydroxide which was shown to cause breakdown of the thiohydantoin amino acids, hydrochloric acid was shown not to destroy the amino acid thiohydantoins. See Scoffone, E., et al., *Ric.Sci.* 26:865-871 (1956); Fox, S. W., et al., *J.Am.Chem. Soc.* 77:3119-3122 (1955); Stark, G. R., *Biochem.* 7:1796-1807 (1968). Cromwell, L. D., et al., *Biochem.* 8:4735-4740 (1969) showed that the concentrated hydrochloric acid could be used to cleave the thiohydantoin amino acid at room temperature. The major drawback with this procedure was that when applied to proteins, no more than two or three cycles could be performed.

Yamashita, S., *Biochem.Biophys.Acta.* 229:301-309 (1971) found that cleavage of peptidylthiohydantoins could be done in a repetitive manner with a protonated cation exchange resin. Application of this procedure to 100 µmol quantities of papain and ribonuclease was reported to give 14 and 10 cycles, respectively, although no details were given. See Yamashita, S., et al., *Proc.Hoshi.Pharm.* 13:136-138 (1971). Stark reported that certain organic bases, such as morpholine or piperidine, could be substituted for sodium hydroxide, and along the same lines, Kubo, H., et al., *Chem.Pharm.Bull.* 19:210-211 (1971) reported that aqueous triethylamine (0.5M) could be used to effectively cleave peptidylthiohydantoins. Stark appeared to have solved the cleavage problem by introducing acetohydroxamic acid in aqueous pyridine at pH 8.2 as a cleavage reagent. This reagent was shown to rapidly and specifically cleave peptidylthiohydantoins at room temperature and at mild pH.

Conditions for the formulation of the peptidylthiohydantoins were improved by Stark and Dwulet, F. E., et al., *Int.J.Peptide and Protein Res.* 13:122-129 (1979), who reported on the use of thiocyanic acid rather than thiocyanate salts, and more recently by the introduction of trimethylsilylisothiocyanate (TMS-ITC) as a coupling reagent. See Hawke, D. H., et al., *Anal.Biochem.* 166:298-307 (1987). The use of this reagent for C-terminal sequencing has been patented. See Hawke U.S. Pat. No. 4,837,165. This reagent significantly improved the yields of peptidylthiohydantoin formation and reduced the number of complicating side products. Cleavage of peptidylthiohydantoins by 12 N HCl (Hawke, 1987) and by acetohydroxamate (Miller, C. G., et al., *Techniques in Protein Chemistry* (Hugli, T. E., ed.) pp. 67-68, Academic Press (1989)) failed to yield more than a few cycles of degradation.

B. The Cleavage Problem

Although the cleavage reaction has been extensively studied since the thiocyanate chemistry for C-terminal degradation was first proposed by Schlack and Kumpf in 1926, a chemical method has not yet been proposed that is capable of an extended degradation. Cleavage in 1N sodium hydroxide as first proposed by Schlack and Kumpf (1926) is well known to hydrolyze proteins and peptides at other sites in addition to cleavage of the C-terminal peptidylthiohydantoin. The released thiohydantoin amino acid derivatives are also known to be unstable in hydroxide solutions. Scoffone, supra. Cleavage by hydroxide is known to convert the side chain amide groups of asparagine and glutamine residues to a carboxylic group making these residues indistinguishable from aspartate and glutamate, respectively.

When cleavage of peptidylthiohydantoins by 12N HCl was applied to proteins and peptides no more than 2 or 3 cycles could be performed. See, Cromwell, supra and Hawke, supra. This was probably due to differences in the rate of hydrolysis of peptidylthiohydantoins containing different amino acid side chains as well as to hydrolysis of other internal amide bonds. Likewise, during the synthesis of the standard amino acid thiohydantoin derivatives corresponding to the naturally occurring amino acids, it was observed that the rate of deacetylation of the N-acetylthiohydantoin amino acids by 12 HCl depended on the nature of the amino acid side chain. Bailey, J. M., et al. *Biochem.* 29:3145-3156 (1990).

Attempts by Dwulet, supra, to reproduce the resin based cleavage method of Yamashita, supra, was reported to be unsuccessful. Cleavage of peptidylthiohydantoins with aqueous methanesulfonic acid was also attempted by Dwulet and by Bailey, et al., both without success. Methanesulfonic acid was chosen since it is equivalent to the acidic group on the resin employed by Yamashita (1971) and Yamashita, et al. (1971).

Cleavage of the peptidylthiohydantoin derivatives with acetohydroxamate as originally reported by Stark, supra, was found to result in the formation of stable hydroxamate esters at the C-terminus of the shortened peptide (Bailey, et al., supra). Depending on the conditions employed, between 68% and 93% of the peptide was derivatized at the C-terminus and thus prevented from further sequencing. Although Stark, supra, predicted such hydroxamate esters to form as an intermediate during cleavage, it was assumed that they would break down under the conditions used for cleavage or continued sequencing. The peptidyl hydroxamate esters formed from cleavage with acetohydroxamate, like the hydroxamate esters studied by Stieglitz, J., et al., *J.Am.-Chem.Soc.* 36:272-301 (1914) and Scott, A. W., et al., *J.Am.Chem.Soc.* 49:2545-2549 (1927), are stable under the acidic conditions used for thiohydantoin formation and can only be hydrolyzed to a free peptidyl carboxylic group, capable of continued sequencing, under strongly basic conditions. This probably explains the low repetitive yields of Stark, supra; Meuth, J. L., et al., *Biochem.* 21:3750-3757 (1982) and Miller, supra, when aqueous acetohydroxamate was employed as a cleavage reagent.

Cleavage of peptidylthiohydantoins by aqueous triethylamine was originally reported by Kubo, H., et al., *Chem.Pharm.Bull.* 19:210-211 (1971), Dwulet, et al., supra, and Meuth, et al., supra. The latter group commented on the usefulness of triethylamine as a cleavage reagent for automated sequencing because of its volatility, but declined to pursue this method apparently in favor of cleavage by acetohydroxamate. Cleavage of peptidylthiohydantoins, in the solution phase, by a 2% aqueous solution of triethylamine was found to be rapid (half-times of 1 min. and 5 min. at 37° C. and 22° C., respectively) and quantitative, yielding only shortened peptide capable of continued sequencing and the amino acid thiohydantoin derivative. Bailey, et al., supra.

SUMMARY OF THE INVENTION

This invention provides novel cleavage reagents, including (i) alkali metal salts of lower trialkylsilanols and (ii) trialkylamine N-oxides. These novel cleavage reagents have particular utility in, but are not limited to, sequencing procedures in which a silyl isothiocyanate is used as the coupling reagent. Sodium trimethyl silanolate and trimethyl amine N-oxide are preferred. Also in the preferred practice of the invention, the peptide or protein sample is covalently coupled to a polyvinyldifluoride (PVDF) membrane or a polyethylene membrane.

DETAILED DESCRIPTION OF THE INVENTION

The mechanism of acid and base hydrolysis of acylthiohydantoins was studied in detail by Congdon and Edward, *Can.J.Chem.* 50:3767-3788 (1972) and a number of cleavage reagents were tested by Stark, supra. Stark found that oxygen containing nucleophiles were the best choice of reagents to effect this reaction. Although acetohydroxamate is an excellent cleavage reagent for the first amino acid, it forms a stable peptidyl hydroxamate ester, which is difficult to remove, and which effectively blocks the shortened peptide from further sequencing. This reagent also results in a high UV absorbing background during subsequent HPLC identification of the released thiohydantoin amino acids. It seems that in general any carbon based reagent that is a good nucleophile and thus a good cleavage reagent will also be a poor leaving group, thereby blocking much of the shortened peptide from further sequencing.

Figure 1:
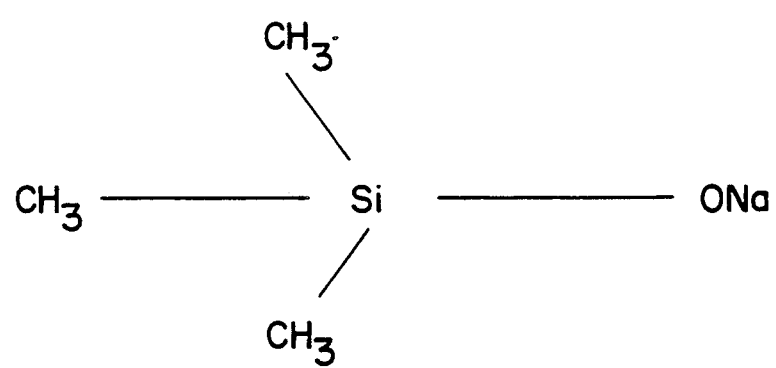
FIG. 1 shows the structural formula for sodium trimethylsilanolate.

Ideally, a cleavage reagent should possess the following characteristics: (1) it should be able to cleave peptidylthiohydantoins in a volatile, water miscible organic solvent, thus eliminating the problems of incompatibility of PVDF membranes with water; (2) the reaction should be rapid and specific; (3) the shortened peptide should be capable of continued degradation; (4) the released thiohydantoin amino acid should not be destroyed by this reagent; and (5) this reagent should not absorb light in the same range as is used for detection of the released thiohydantoin amino acid derivatives. Sodium trimethylsilanolate (FIG. 1), commercially available from Petrarch (Huls), in, e.g., alcoholic solvents, and trimethyl amine N-oxide (FIG. 5) commercially available from Aldrich Chemical Co. in alcoholic and a wider range of solvents seem to possess all of these characteristics. Cleavage of peptidylthiohydantoins in the solution phase with a 0.05M solution of sodium trimethylsilanolate in 100% methanol or trimethylsilylethanol is complete in less than 5 minutes. A 0.05M solution of sodium trimethylsilanolate in methanol or trimethylsilylethanol effects cleavage of peptidylthiohydantoins both in the solution phase and in the solid phase in less than 5 minutes.

More specifically, this invention contemplates the use of the cleavage reagents of this invention in a concentration of from about 0.025 molar to about 0.25 molar, preferably from about 0.1 to about 0.2 molar, in methanol, trimethylsilylethanol or similar alcohols or, in the case of trimethylamine N-oxide, a wider range of solvents, such as alkanols having 1 to about 4 carbon atoms.

Figure 2:
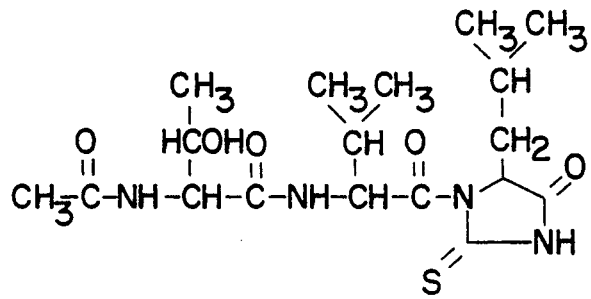
FIG. 2 shows a possible mechanism for the cleavage of the peptidyl thiohydantoin using sodium trimethylsilanolate.
Figure 2:
Figure 2:
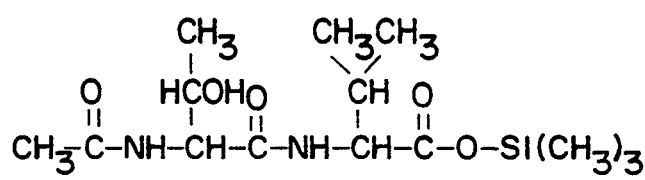
Figure 2:
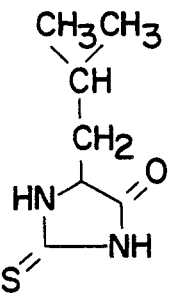
Figure 2:
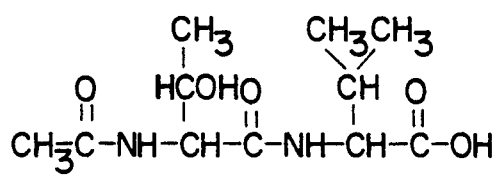

The most probable mechanism of this cleavage involves formation of an unstable C-terminal trimethylsilyl ester which, in the presence of water or alcohol, rapidly reforms the desired C-terminal carboxylic group (FIG. 2).

FIG. 2 illustrates the use of aqueous trifluoroacetic acid (TFA) following the cleavage reaction. Preferably, the concentration of TFA in this step is from about 0.01M to about 0.2M. The use of TFA or an equivalent acid at this stage significantly facilitates cleavage.

Standard techniques are utilized for coupling the peptide to PVDF or to another membrane. A PVDF membrane or the like of appropriate size is placed in the continuous flow reactor described in Shively, Ser. No. 07/072,754, filed July 13, 1987, now pending, and activated by treatment for about two hours with 2 μL of 1,3-dicyclohexylcarbodiimide (2 mM/mL) in N,N-dimethylformamide (DMF). The activated membrane is washed with two mL of DMF and dried under a stream of argon. The peptide sample in solution in DMF is layered on the dry membrane and allowed to react overnight. The membrane is then washed with methanol and dried under a stream of argon.

Use of this new reagent for cleavage in trimethylsilylethanol as a solvent has allowed the automated C-terminal sequencing of four cycles, each for both YGGFL and KVILF covalently coupled to PVDF. The fifth residue, Y and K, respectively, could not be sequenced as this is the residue which is used for covalently attaching the peptides to the PVDF. Although trimethylsilyl ethanol is a good solvent for cleavage, it may not be an ideal solvent because of its high boiling point and insolubility with water. Other alcoholic solvents useful in the invention include alkanols having from one to about four atoms, e.g., methanol, ethanol, isopropanol and isobutanol.

In its more broad aspects, the invention includes cleavage reagents having the formula $R_3SiO^-X^+$, in which R is a straight or branched chain hydrocarbon radical having from about 1 to about 10 carbon atoms and X is an alkali metal ion, preferably a sodium or a potassium ion.

The broader aspects of the invention also include trimethylamine N-oxides in which the alkyl groups have from one to about four carbon atoms. Triethyl, tripropyl, triisopropyl, tributyl or triisobutyl amine N-oxides may be used. Such reagents have the formula $(R_1)_3 N^+—O^-$, in which $R_1$ is an alkyl group having from one to about four carbon atoms.

EXEMPLIFICATION OF THE INVENTION

The examples described herein illustrate C-terminal sequencing accomplished with a modified N-terminal sequencer based on the design of Hawke, et al., *Anal.Biochem.* 147:315-330 (1985), in which a continuous flow reactor as described in Shively U.S. patent application Ser. No. 072,754 was utilized. Release of thiohydantoin amino acids was detected by an on-line HPLC. See Shively, *Anal.Biochem.* 163:517-529 (1987). The reagent and solvent delivery system were all constructed from perfluoroelastomers. Delivery valves as generally described in U.S. Pat. No. 4,530,586 provided with electromagnetically actuated solenoids and zero dead volume were connected in a modular fashion providing multiple input to a single output line. The valves which control the flow of reagents and solvents are computer operated pursuant to a program appropriate for the chemistry involved.

EXAMPLE 1

Sequencing of Leucine Enkephalin (YGGFL) (1.2 nmoL) Covalently Coupled to PVDF

The thiohydantoin amino acid derivatives were separated by reverse phase HPLC. This separation was performed on Phenomenex Ultracarb 5 ODS(30) column (2.0 mm×25 mm) on a Beckman System Gold with a Shimadzu (SPD-6A) detector. The column was eluted for 2 min with solvent A (0.1% trifluoroacetic acid in water) and then followed by a discontinuous gradient to solvent B (80% acetonitrile, 10% methanol in water) at a flow rate of 0.15 mL/min at 22° C. The gradient used was as follows: 0% B for 2 min, 0-6% B over 3 min, 6-35% B over 35 min, 35-50% B over 10 min, and 50-0% B over 10 min.

TABLE 1

| Composition of Reagents and Solvents | |
|---|---|
| R1 | Acetic anhydride |
| R2 | 30% TMS-ITC in acetonitrile |
| R3 | 0.05M Sodium trimethylsilanolate in 2-trimethylsilylethanol |
| R4 | Methanol |
| S1 | Acetonitrile |
| S2 | 0.8% Trifluoroacetic acid in water |
| S3 | Methanol |
| S4 | — |

TABLE 2

| C-Terminal Sequencer Program Summary | | | |
|---|---|---|---|
| Continuous Flow Reactor (CFR) (70° C.) | Conversion Flask (CF) (50° C.) | Duration (min) | Total Time (min) |
| Dry | Dry | 3.0 | 3.0 |
| R1 reaction | | 5.0 | 8.0 |
| R1 reaction | | 5.0 | 13.0 |
| S1 rinse | | 0.5 | 13.5 |
| R2 reaction | | 10.0 | 23.5 |
| S1 rinse | | 1.0 | 24.5 |
| R2 reaction | | 10.0 | 34.5 |
| S1 rinse | | 1.0 | 35.5 |
| R2 reaction | | 10.0 | 45.5 |
| S3 rinse | | 1.0 | 46.5 |
| S1 rinse | | 1.0 | 47.5 |
| S1 rinse | | 1.0 | 48.5 |
| S1 rinse | | 1.0 | 49.5 |
| R3 reaction | | 10.0 | 59.5 |
| R3 to CF | | 0.5 | 60.0 |
| | Dry | 10.0 | 70.0 |
| | R4 delivery | 0.2 | 70.2 |
| | Dry | 8.3 | 78.5 |
| | R4 delivery | 0.2 | 78.7 |
| | Dry | 8.3 | 87.0 |
| S2 delivery | | 0.1 | 87.1 |
| S2 reaction | | 0.5 | 87.6 |
| S2 to CF | | 0.5 | 88.1 |
| S2 delivery | | 0.1 | 88.2 |
| S2 reaction | | 0.5 | 88.7 |
| S2 to CF | | 0.5 | 89.2 |
| | inject | 1.0 | 90.2 |
| S3 rinse | | 1.0 | 91.2 |
| S1 rinse | | 1.0 | 92.2 |
| S1 rinse | | 1.0 | 93.2 |
| S1 rinse | | 1.0 | 94.2 |
| | R4 rinse | 1.0 | 95.2 |

Figure 3:
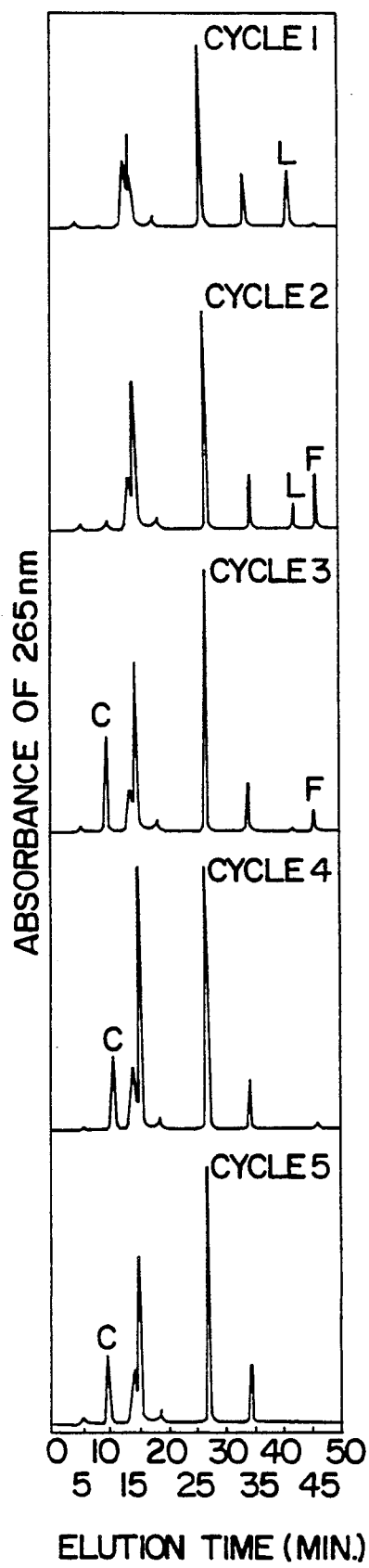
FIG. 3 shows the HPLC analysis of the products of Example 1.

FIG. 3 depicts the HPLC analysis of products of the reaction.

EXAMPLE 2

Sequencing of KVILF (1.2 nmoL) Covalently Coupled to PVDF

The thiohydantoin amino acid derivatives were separated by reverse phase PHLC. This separation was performed on Phenomenex Ultracarb 5 ODS(30) column (2.0 mm×25 mm) on a Beckman System Gold with a Shimadzu (SPD-6A) detector. The column was eluted for 2 min with solvent A (0.1% trifluoroacetic acid in water) and then followed by a discontinuous gradient to solvent B (80% acetonitrile, 10% methanol in water) at a flow rate of 0.15 mL/min at 22° C. The gradient used was as follows: 0% B for 2 min, 0-6% B over 3 min, 6-35% B over 35 min, 35-50% B over 10 min, and 50-0% B over 10 min.

TABLE 3

| Composition of Reagents and Solvents | |
| --- | --- |
| R1 | Acetic anhydride |
| R2 | 30% TMS-ITC in acetonitrile |
| R3 | 0.05M Sodium trimethylsilanolate in methanol |
| R4 | Methanol |
| S1 | Acetonitrile |
| S2 | 0.8% Trifluoroacetic acid in water |
| S3 | — |
| S4 | — |

TABLE 4

C-Terminal Sequencer Program Summary

| Continuous Flow Reactor (CFR) (70° C.) | Conversion Flask (CF) (50° C.) | Duration (min) | Total Time (min) |
| --- | --- | --- | --- |
| Dry | Dry | 3.0 | 3.0 |
| R1 reaction | | 5.0 | 8.0 |
| R1 reaction | | 5.0 | 13.0 |
| S1 rinse | | 0.5 | 13.5 |
| R2 reaction | | 10.0 | 23.5 |
| S1 rinse | | 1.0 | 24.5 |
| R2 reaction | | 10.0 | 34.5 |
| S1 rinse | | 1.0 | 35.5 |
| R2 reaction | | 10.0 | 45.5 |
| S1 rinse | | 1.0 | 46.5 |
| S1 rinse | | 1.0 | 47.5 |
| S1 rinse | | 1.0 | 48.5 |
| R3 reaction | | 5.0 | 53.5 |
| R3 to CF | | 0.5 | 54.0 |
| | Dry | 3.0 | 57.0 |
| | R4 delivery | 0.2 | 57.2 |
| | Dry | 5.0 | 62.2 |
| S2 delivery | | 0.1 | 62.3 |
| S2 reaction | | 3.0 | 65.3 |
| S2 to CF | | 0.5 | 65.8 |
| S2 delivery | | 0.1 | 65.9 |
| S2 reaction | | 3.0 | 68.9 |
| S2 to CF | | 0.5 | 69.4 |
| | inject | 1.0 | 70.4 |
| S1 rinse | | 1.0 | 71.4 |
| S1 rinse | | 1.0 | 72.4 |
| S1 rinse | | 1.0 | 73.4 |
| | R4 rinse | 1.0 | 74.4 |

Figure 4:
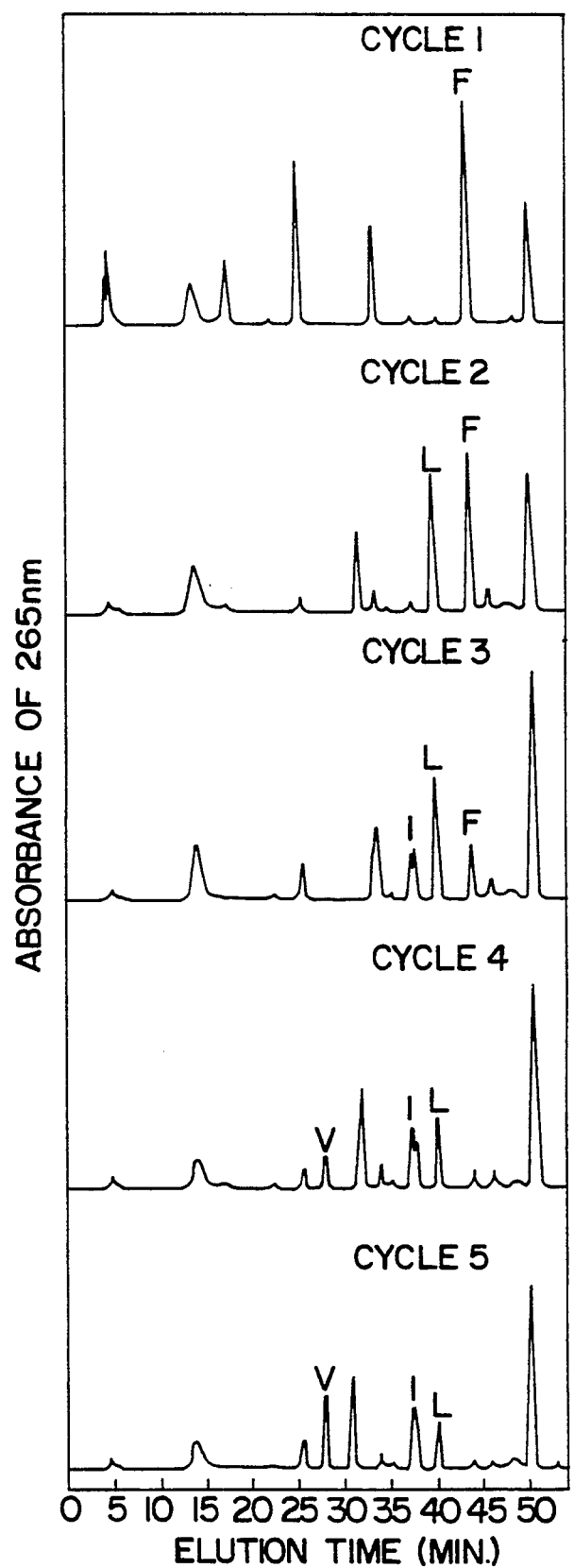
FIG. 4 shows the HPLC analysis of the products of Example 2.

FIG. 4 depicts the HPLC analysis of the products of the reaction.

Figure 5:
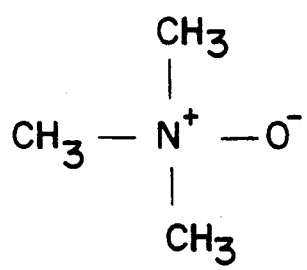
FIG. 5 shows the structural formula for trimethylamine N-oxide.

FIG. 5 is the formula of trimethyl amine N-oxide.

Figure 6:
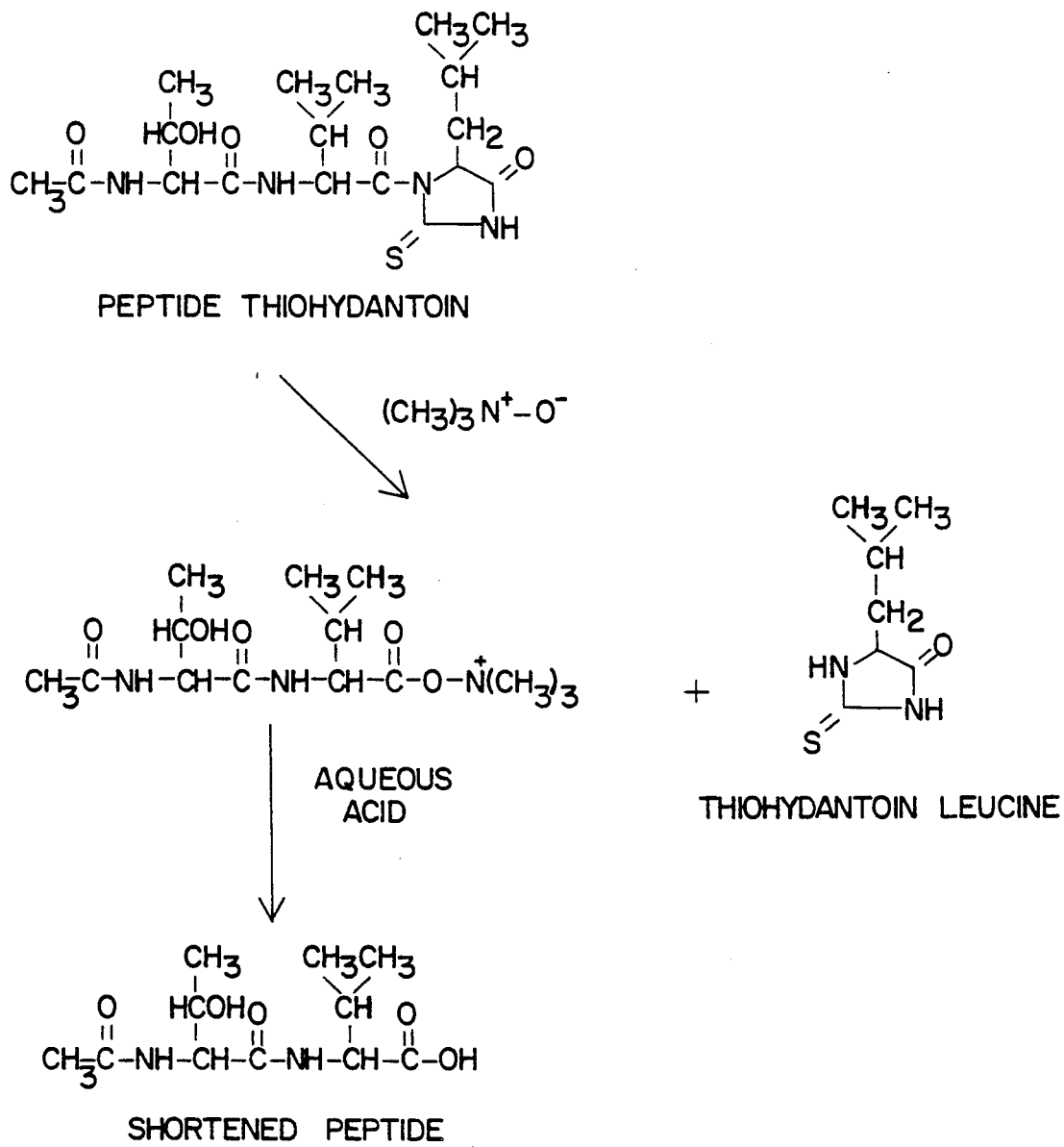
FIG. 6 shows a possible mechanism for the cleavage of the peptidyl thiohydantoin using trimethylamine N-oxide.

FIG. 6 depicts the most probable mechanism of a cleavage reaction involving trimethylamine N-oxide and the use of aqueous acid following the cleavage reaction.

What is claimed is:

1. A method for sequencing a peptide by carboxyl terminal degradation which comprises coupling the carboxyl terminus of a peptide with a silyl isothiocyanate coupling reagent to form a peptidylthiohydantoin derivative and cleaving the peptidylthiohydantoin derivative with sodium trimethylsilanolate or trimethylamine N-oxide to provide a thiohydantoin derivative of the amino acid previously at the carboxyl terminus of the peptide and a peptidyl residue lacking such an amino acid.

2. The method as defined by claim 1 in which the peptide is coupled to a polyvinyldifluoride or a polyethylene membrane.

3. A method as defined by claim 1 or claim 2 in which said cleaving of said peptidylthiohydantoin is conducted in a solvent selected from the group consisting of alkanols having from 1 to about 4 carbon atoms and trimethylsilylethanol.

4. A method as defined by claim 1 or claim 2 in which said silylisothiocyanate is trimethylsilylisothiocyanate.

5. A method for sequencing a peptide by carboxyl terminal degradation which comprises coupling the carboxyl terminus of a peptide with a silyl isothiocyanate coupling reagent to form a peptidylthiohydantoin derivative and cleaving the peptidylthiohydantoin derivative with a reagent having the formula $R_3SiO^-X^+$, in which R is a straight or branched chain hydrocarbon radical having from about 1 to about 10 carbon atoms and X is an alkali metal ion or the formula $(R_1)_3N^+-O^-$, in which $R_1$ is an alkyl group having from one to about four carbon atoms to provide a thiohydantoin derivative of the amino acid previously at the carboxyl terminus of the peptide and a peptidyl residue lacking such an amino acid.

6. The method as defined by claim 5 in which the peptide is coupled to a polyvinyldifluoride or polyethylene membrane.

7. A method for sequencing a peptide by carboxyl terminal degradation which comprises coupling the carboxyl terminus of a peptide with a coupling reagent to form a peptidylthiohydantoin derivative and cleaving the peptidylthiohydantoin derivative with a reagent having the formula $R_3SiO^-X^+$, in which R is a straight or branched chain hydrocarbon radical having from about 1 to about 10 carbon atoms and X is an alkali metal ion to provide a thiohydantoin derivative of the amino acid previously at the carboxyl terminus of the peptide and a peptidyl residue lacking such an amino acid.

* * * * *